(12) United States Patent
Sedlacek et al.

(10) Patent No.: US 6,358,732 B1
(45) Date of Patent: *Mar. 19, 2002

(54) DNA FOR EXPRESSION UNDER CONTROL OF A CELL CYCLE-DEPENDENT PROMOTER

(75) Inventors: Hans-Harald Sedlacek; Rolf Müller, both of Marburg (DE)

(73) Assignee: Aventis Pharma Deutschland GmbH, Frankfurt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/793,110

(22) PCT Filed: Aug. 25, 1995

(86) PCT No.: PCT/EP95/03369

§ 371 Date: Apr. 25, 1997

§ 102(e) Date: Apr. 25, 1997

(87) PCT Pub. No.: WO96/06939

PCT Pub. Date: Mar. 7, 1996

(30) Foreign Application Priority Data

Aug. 26, 1994 (GB) ............................................... 9417366
Mar. 29, 1995 (GB) ............................................... 9506466

(51) Int. Cl.[7] ........................ C12N 15/85; C12N 15/86; C07H 21/04; A61K 48/00
(52) U.S. Cl. .................... 435/320.1; 424/93.2; 435/375; 435/455; 514/44; 536/23.1; 536/23.5; 536/24.1
(58) Field of Search .......................... 514/44; 435/320.1, 435/375, 172.3, 455; 424/93.2; 536/23.1, 23.5, 24.1

(56) References Cited

U.S. PATENT DOCUMENTS

| 5,830,880 A | 11/1998 | Sedlacek et al. ............... 514/44 |
| 5,854,019 A | 12/1998 | Sedlacek et al. ........... 435/69.1 |
| 5,885,833 A | 3/1999 | Mueller et al. ............. 435/372 |
| 5,916,803 A | 6/1999 | Sedlacek et al. ......... 435/320.1 |

OTHER PUBLICATIONS

Marshall, E (1995) Science 269: 1050–1055.*
Miller et al (1995) FASEB J. 9 : 190–199.*
Crystal R.G. (1995) Science 270: 404–410.*

* cited by examiner

*Primary Examiner*—Scott D. Priebe
(74) *Attorney, Agent, or Firm*—Heller Ehrman White & McAuliffe

(57) ABSTRACT

A DNA sequence is disclosed for the genetic therapy of diseases of the central nervous system. The essential components for the DNA sequence are the activator sequence, the promoter module, and the active substance coding gene. The activator sequence is specifically activated in activated endothelial or glial cells. Activation is cell cycle-regulated by the promoter module. The active substance represents an inhibitor of the nerve growth factor, a dopanine metabolism enzyme, and/or a nerve cell protection factor. The disclosed DNA sequence is inserted into a viral or non-viral vector, supplemented with a ligand with affinity for the target cells.

16 Claims, 6 Drawing Sheets

FIG. 1

```
       C290↓
-310   TTCGTGGGCTGAGGGAACGAGGAAAAACAGAAAGGGTGTGGAGATTGG TGAGAGGGAGAGCCAATGATGCCAG
            CBS9                                                                •
             •••                                                                G
             °°°
-235   GCTCCCCGTGAGAGGCGGAGCTTACCCCGCAGCCTGCCTAACGCTGGTGGGCCAAACACTAT CTGCTCTGGCTATG
                G   G G    °                                                GG
                •   ° •                                                     °°
                                        CBS7
                                       ←    →                              CBS6    CBS5
-160   GCTCCCCGTGAGAGGCGGAGCTTACCCCGCAGCCTGCCTAACGCTGG       CAAGCACAAGCACAAGCGCCCCCAGGTGATC TGGGAGCCAAGGATAGGCCATG
       CBS8 [Sp1]                              G G GGGGG                          °°
        ••••••                                 • • • •••                          ••
        °°°°°°
              C74↓ CBS4  CBS3                                                           CDE
                                                                       CBS2  CBS1      ***
-85    AGGCCCTGGGGCGGGGGGAGATTGG CTGACGCAGCTTAGAGGCCGAGCGGGGATAGG TTACTGGGCTGGGGGA
       ■START 1                                                       C20↓            G*
-10    AGGTTTGAATGGTCAACGCCTGCGGGCTGTTGATATTCTTGCTCAGAGGCCGTAACTTTGGCCTTCTGCTCAGGGA
       ■START 2
```

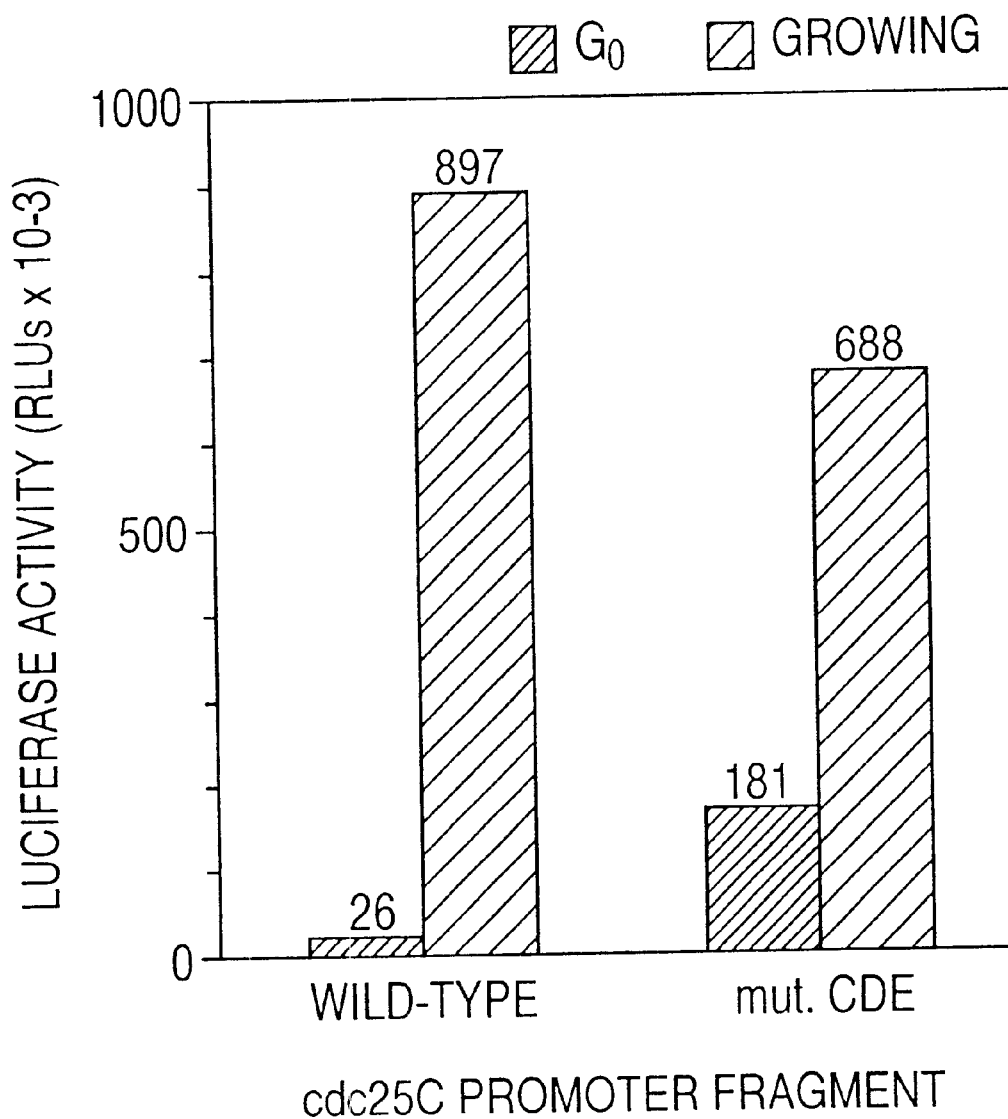

MULTIPLE NON-SPECIFIC ENHANCER ELEMENTS

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:1:

GCGCGCGGAG ATTGGCTGAC G                                              21

(2) INFORMATION FOR SEQ ID NO:2:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:2:

GGCGAGCGGG GATAGGT                                                   17

(2) INFORMATION FOR SEQ ID NO:3:

(i) SEQUENCE CHARACTERISTICS:
       (A) LENGTH: 21 base pairs
       (B) TYPE: nucleic acid
       (C) STRANDEDNESS: single -continued (D) TOPOLOGY: linear (xi) SEQUENCE DESCRIPTION: SEQ ID NO:3:

CTGGGGTCTG ATTGGCTGCT T                                         21

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:4:

CGGGCTACCC GATTGGT                                              17

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

CTGTCGCCTT GAATGACGTC A                                         21

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:6:

CGAGCGCTTT CATTGGT                                              17

(2) INFORMATION FOR SEQ ID NO:7:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (xi) SEQUENCE DESCRIPTION: SEQ ID NO:7:

TTCGTGGGGC TGAGGGAACG AGGAAAACAG AAAGGGTGTG GAGATTGGTG A GAGGGAGAG    60

CCAATGATGC GCCAGGCTCC CCGTGAGGCG GAGCTTACCC CGCAGCCTGC C TAACGCTGG   120

TGGGCCAAAC ACTATCCTGC TCTGGCTATG GGGCGGGGCA AGTCTTACCA T TTCCAGAGC   180

AAGCACACGC CCCCAGGTGA TCTGCGAGCC CAACGATAGG CCATGAGGCC C TGGGCGCGC   240

GCGCGGAGAT TGGCTGACGC AGCTTAGAGG CGAGCGGGGA TAGGTTACTG G GCTGGCGGA   300

AGGTTTGAAT GGTCAACGCC TGCGGCTGTT GATATTCTTG CTCAGAGGCC G TAACTTTGG   360

CCTTCTGCTC AGGGA                                                    375

DNA FOR EXPRESSION UNDER CONTROL OF A CELL CYCLE-DEPENDENT PROMOTER

TECHNICAL FIELD

A DNA sequence is described for the gene therapy of diseases of the central nervous system.

The essential elements of this DNA sequence are the activator sequence, the promoter module and the gene for the active substance.

The activator sequence is activated, in a cell-specific manner, in activated endothelial cells or glial cells. This activation is regulated by the promoter module in a cell cycle-specific manner. The active substance is a nerve growth factor, an enzyme of dopanine metabolism and/or a protective factor for nerve cells. The described DNA sequence is inserted into a viral or non-viral vector which is supplemented by a ligand having affinity for the target cell.

1. THE CENTRAL NERVOUS SYSTEM AND GROWTH FACTORS

After the conclusion of ontogenesis, the nerve cells constitute cells which are fully differentiated and no longer capable of division. In general, they are characterized by the nerve cell body and nerve cell processes, with a distinction being made between afferent (dentrites) and efferent (neurites) processes. The efferent neurite, only one of which is generally formed per nerve cell, makes contact with its target organ (nerve cells or other types of somatic cell) by way of synapses.

Maintenance of the anatomical structure and function of nerve cells is effected in the presence of neuronal growth factors.

In a general sense, neuronal growth factors are to be understood as being neurotrophic factors (Reviews in Massague, *Cell* 49, 437 (1987), Pusztai et al., J. Pathol. 169, 191 (1993), Ibanez et al., *PNAS* 89, 3060 (1992), Sonoda et al., BBRC 185, 103 (1992)). These factors include neuronal growth factors in Table 1.

In a narrower sense, the nerve growth factor (NGF) family should be included in these factors.

NGFs act by way of binding to NGF receptors, which are formed, in particular, on the sensory nerve fibers. NGF is taken up intracellularly and transported to the nerve cell body in a retrograde manner (Johnson et al., *J. Neurosci.* 7, 923 (1987)). In the nerve cell body, the NGF probably brings about an increase in cyclic adenosine monophosphate (cAMP), with subsequently elevated efflux of $Ca^{++}$ (Schubert et al., *Nature* 273, 718 (1978), and, in addition, release of diacylglycerol and activation of protein kinase C, by way of inositol lipid metabolism, and intracellular release of $CA_{++}$ by way of inositol triphosphate liberation (Abdel-Latif, *Pharmacol. Rev.* 38, 227 (1986)).

The phosphorylation of specific, in particular signal-transducing, proteins which results from this leads to changes in their function. This results in an increased formation of proteins which are involved in the growth of neurites. These proteins include chartin proteins (Black et al., *J. Cell Biol.* 103, 545 (1986)) tau proteins and tubulins (Drubin et al., *J. Cell Biol.* 101, 1799 (1985)). Thus, the synthesis of α-tubulins and β-tubulins, neuro-filament proteins (NF-L, NF-M and NF-H) and peripherin (Portier et al., *Devi Neuroscience* 6, 215 (1983)), Parysek et al., *J Neurosci.* 7, 78, (1987)) is elevated. At the same time, the concentration of enzymes which are important in the nervous system, such as choline acetyl-transferase, acetylcholinesterase and neurone-specific enolase (Vinores et al., *J. Neurochemistry* 37, 597, 1981), Rydel et al., J. Neurosci. 7, 3639 (1987)) increases.

In addition, the concentrations of neurotransmitters, such as neurotensin (Tischler et al., Reg. Pept. 3, 415 (1982)) and neuropeptide Y (Allen et al., *Neurosci. Lett.* 46, 291 (1984)), and neurotransmitter receptors, such as acetylcholine receptors (Mitsuka et al., *Brain Res.* 314, 255 (1984)) and encephalin receptors (Inoue et al., *J. Biol. Chem.* 257, 9238 (1982)) are increased. At the same time, the concentration of synapsin 1 is increased (Romano et al., *J. Neurosci.* 7, 1300 (1987)).

In the final analysis, NGF maintains the functional state of nerve cells. At the same time, NGF initiates and promotes the growth of neurites. The constant presence of NGF is necessary for this neuritogenic and synaptogenic activity (Smith, *Science* 242, 708 (1988), Mitchison et al., *Neuron* 1, 761 (1988)).

This has been reported, in particular, for ciliary neurotrophic factor (CNTF) (Lin et al., *Drugs of the Future* 19, 557 (1994)).

The neurotrophic activity of neuronal growth factors has been substantiated experimentally, in particular in association with damage to nerve cells, for example in association with the surgical severence of neurites. If CNTF is administered locally to the proximal stump of the transected nerves, the proportion of nerve cells which die following the surgical intervention is markedly reduced (Sendtner et al., *Nature* 345, 440 (1990)). At the same time, the concentration of, for example, the neuro-peptide substance P is markedly elevated in the spinal ganglia following CNTF administration. Rats whose sciatic nerve has been damaged exhibit accelerated restoration of the motor activity following subcutaneous administration of CNTF (Lin et al., *Drugs of the Future* 19, 557 (1994)).

However, systemic administration of neurotrophic factors is only effective if the motor neurones, which are present in the spinal cord and which are protected by the blood-brain barrier, possess axons which are still functional outside these barriers and by way of which the neurotrophic factors can be taken up (Apfel et al., Brain Res. 605 1 (1993)).

In the case of nerve cell damage up to the other side, or on the other side, of the blood-brain barrier, it is necessary to administer neurotrophic factors intracranially. In this way, retrograde generation of the proximal thalamic neurones following severance of the thalamic axons can, for example, be prevented experimentally (Clatterbuch et al., PNAS 90, 2222 (1993)). However, a prerequisite for an optimal regeneration process is the constant presence of the neutrophic factors at the site of the damaged nerve cell. While it is possible to effect a local administration at the time of the surgical damage or damage relief, this is difficult, or almost impossible to do once the surgical intervention has ended. Diffuse damage to the CNS, for example due to blunt trauma or toxins, affords only very limited opportunity for effecting a targeted administration.

Glial cells can be stimulated to produce TNF as a result of traumatic, immunological and toxic influences. This TNF α is, at that time, toxic for nerve cells and glial cells, (Owens et al., Immunol. Today 15, 566 (1994)).

In order to achieve a presence of active compounds in the CNS which is as long-term as possible, attempts are made to inject intracranially cells (fibroblasts, endothelial cells and myoblasts) which have been transduced in vitro to express neurotrophic active compounds. The aim is to use the neurotrophic active compounds to improve the regeneration and function of nerve cells which have been damaged traumatically or degeneratively, for example in Parkinson's disease or in dementia. Especially in the case of Parkinson's disease, attempts are made to inject cells, which either have been transduced in vitro, to secrete neurospecific enzymes such as tyrosine hydroxylase and dopa decarboxylase (Kopin, *Ann. Rev. Pharmacol. Toxicol.* 32, 467 (1993), Fisher et al., *Physiol. Rev.* 11, 582 (1993), Jiao et al., *Nature* 362, 450 (1993)), or else human fetal, dopaminergic, nigral neurones are injected (Löwenstein, *Bio/Technology* 12, 1075 (1994)).

However, cells of this nature are only available in limited quantities. On the other hand, the use of fetal cells raises important ethical questions.

As an alternative, the possibility is being examined of injecting vectors directly into the brain in order to transduce brain cells to express the desired active compounds (During et al., *Science* 266, 1399 (1994)). However since these vectors do not exhibit any cell specificity, there is the substantial risk of nerve cells being damaged by infection or transfection with the vector.

BRIEF DESCRIPTION OF THE DRAWINGS

FIG. 1: Nucleotide sequence of the cdc25C promoter region showing the protein binding sites (genomic DMS footprinting; • (filled circles): complete constitutive protection; ○ (open circle): partial constitutive protection; * (asterisk): cell cycle-regulated, G1-specific protection) which were found in vivo. CBS: constitutive binding site; CDE: cell cycle-dependent element. Regions which are underlaid in gray indicate the $Y_c$ boxes (NF-Y binding sites). Start sites are labelled by filled squares. SEQ ID NO:7 is shown in this Figure.

FIG. 2: Depression of the cdc25C promoter specifically in $G_0$ by means of mutating the cdc.

2. DESCRIPTION OF THE INVENTION

Figure 3:
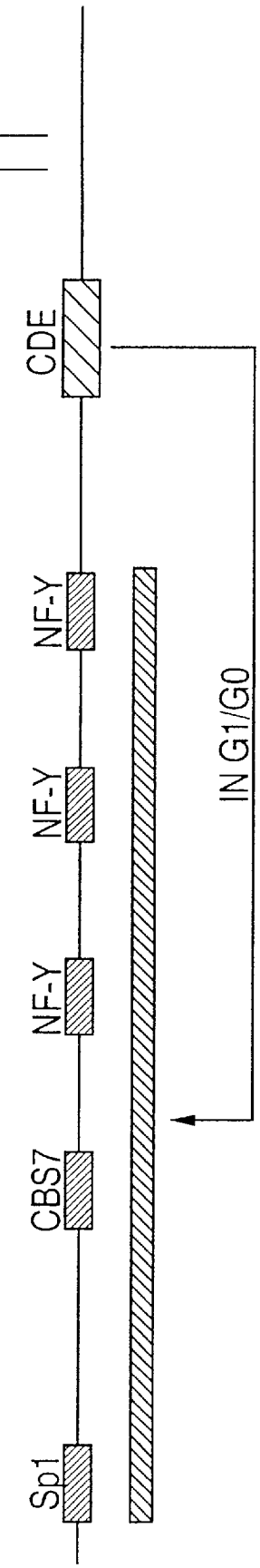
FIG. 3: Diagrammatic representation of the regulation of the cdc25C enhancer by the CDE.

The present invention now relates to an active compound which can be administered both locally and systemically to patients as a pharmaceutical and by means of which neuro-specific factors are produced over a relatively long period at the site of the nerve cell damage. Neuro-specific factors of this nature can be neurotrophic factors which protect nerve cells from further damage and bring about regeneration of nerve cells. However, neuro-specific factors can also be enzymes, such as tyrosine hydroxylase and dopa decarboxylase, which are responsible for synthesizing dopamine from tyrosine. In addition, neurospecific factors can be substances which inhibit or neutralize TNFα.

The central component of this active compound is a DNA construct which is composed of the following elements:

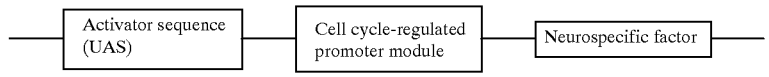

(In the entire text of this application, DNA is used as a common term for both a complementary (cDNA) sequence and a genomic DNA sequence).

2.1. Choice of the Activator Sequence

An activator sequence (UAS=upstream activator sequence) is to be understood as being a nucleotide sequence (promoter sequence or enhancer sequence) with which transcription factors interact which are formed or are active in endothelial cells or glial cells.

The CMV enhancer or CMV promoter (EP-B1-0 173 177), or the SV40 promoter, or any other promoter sequence or enhancer sequence which is known to the skilled person, can be used as the activator sequence.

However, within the meaning of this invention, the preferred activator sequences include gene-regulatory sequences or elements from genes which encode proteins which are formed, in particular, in endothelial cells or glial cells.

a) Activator Sequences which are Activated in Endothelial Cells

Some of these proteins have been described by Burrows et al. (*Pharmac. Therp.* 64, 155 (1994) and Plate et al. (*Brain Pathol.* 4, 207 (1994)). In particular, these endothelial cell-specific proteins include, for example:

Brain-specific, endothelial glucose-1 transporter Endothelial cells of the brain express this transporter very strongly for the purpose of achieving the transendothelial transport of D glucose into the brain (Gerhart et al., *J. Neurosci. Res.* 22, 464 (1989)). The promoter sequence has been described by Murakami et al. (*J. Biol. Chem.* 267, 9300 (1992)).

Endoglin

Endoglin appears to be a TGFβ receptor which is not signal-transmitting (Gangos et al., *J. Biol. Chem.* 265, 8361 (1990), Moren et al., *BBRC* 189, 356 (1992), Cheifetz, J. Biol. Chem. 267, 19027 (1992)). While it is present in small quantities on normal endothelium, it is expressed more strongly on proliferating endothelium (Westphal et al., *J. Invest. Derm.* 100, 27 (1993), Burrows et al., *Pharmac. Ther.* 64, 155 (1994)). The promoter sequences have been described by (Bellon et al., *Eur. J. Immunol.* 23, 2340 (1993), Ge et al., *Gene* 138, 201 (1994)).

VEGF receptors

Two receptors are distinguished (Plate et al., *Int. J. Cancer* 59, 520 (1994)).

VEGF receptor 1 (flt-1) (de Vries et al., *Science* 255, 989 (1992)) contains an fms-like tyrosine kinase in the cytoplasmic moiety, and VEGF receptor 2 (flk-1, KDR) (Terman et al., BBRC 187, 1579 (1992)) contains a tyrosine kinase in the cytoplasmic moiety.

Both receptors are found almost exclusively on endothelial cells (Senger et al., *Cancer Metast. Rev.* 12, 303 (1993)).

Other endothelium-specific receptor tyrosine kinases til-1 or til-2 (Partanen et al., *Mol. Cell Biol.* 12, 1698 (1992), Schnürch and Risau, *Developm.* 119, 957 (1993), Dumont et al., *Oncogene* 7, 1471 (1992))

B61 receptor
(Eck receptor) (Bartley et al., *Nature* 368, 558 (1994), Pandey et al., *Science* 268, 567 (1995), Van der Geer et al., *Ann. Rev. Cell Biol.* 10, 251 (1994))

B61
The B61 protein is the ligand for the B61 receptor. (Holzman et al., *J. Am. Soc. Nephrol.* 4, 466 (1993), Bartley et al., *Nature* 368, 558 (1994))

endothelin, in particular
Endothelin B (Oreilly et al., *J. Cardiovasc. Pharm.* 22, 18 (1993), Benatti et al., *J. Clin. Invest.* 91, 1149 (1993), O'Reilly et al., *BBRC* 193, 834 (1993)). The promoter sequence has been described by Yanasigawa et al., *Nature* 332, 411 (1988) and Benatti et al., *J. Clin. Invest.* 91, 1149 (1993).
endothelin-1 (Yanasigawa et al., *Nature* 332, 411 (1988)). The promoter sequence has been described by Wilson et al., *Mol. Cel. Biol.* 10, 4854 (1990).
endothelin receptors, in particular the endothelin B receptor (Webb et al., *Mol. Pharmacol.* 47, 730 (1995), Haendler et al., *J. Cardiovasc. Pharm.* 20, 1 (1992)).

Mannose 6-phosphate receptors
(Perales et al., *Eur. J. Biochem.* 226, 225 (1994), Dahms et al., *Cell* 50, 181 (1987)).
The promoter sequences have been described by Ludwig et al., (*Gene* 142, 311 (1994)), Oshima et al., (*J. Biol. Chem.* 263, 2553 (1988)) and Pohlmann et al. (*PNAS USA* 85, 5575 (1987)).

von Willebrand factor
The promoter sequence has been described by Jahroudi and Lynch (*Mol. Cell. Biol.* 14, 999 (1994), Ferreira et al., *Biochem. J.* 293, 641 (1993) and Aird et al., *PNAS USA* 92, 4567 (1995)).

IL-1α and IL-1β
IL-1 is produced by activated endothelial cells (Warner et al., *J. Immunol.* 139, 1911 (1987). The promoter sequences have been described by Hangen et al., *Mol. Carcinog.* 2, 68 (1986), Turner et al., *J. Immunol.* 143, 3556 (1989), Fenton et al., *J. Immunol.* 138, 3972 (1987), Bensi et al., *Cell Growth Diff.* 1, 491 (1990), Mori et al., *Blood* 84, 1688 (1994), Hiscott et al., *Mol. Cell. Biol.* 13, 6231 (1993).

IL-1 receptor
The promoter sequence has been described by Ye et al., *PNAS USA* 90, 2295 (1993).

Vascular cell adhesion molecule (VCAM-1)
The expression of VCAM-1 in endothelial cells is activated by lipopolysaccharides, TNF-α (Neish et al., *Mol. Cell. Biol.* 15, 2558 (1995)), IL-4 (Iademarco et al., *J. Clin. Invest.* 95, 264 (1995)), IL-1 (Marni et al., *J. Clin. Invest.* 92, 1866 (1993)).
The promoter sequence of VCAM-1 has been described by Neish et al., *Mol. Cell. Biol.* 15, 2558 (1995), Ahmad et al., *J. Biol. Chem.* 270, 8976 (1995), Neish et al., *J. Exp. Med.* 176, 1583 (1992), Iademarco et al., *J. Biol. Chem.* 267, 16323 (1992) and Cybulsky et al., *PNAS USA* 88, 7859 (1991).

Synthetic activator sequences
Synthetic activator sequences, which are composed of oligomerized binding sites for transcription factors which are preferentially or selectively active in endothelial cells, can also be used as an alternative to natural endothelium-specific promoters. An example of these synthetic activator sequences is transcription factor GATA-2, whose binding site in the endothelin-1 is gene ... TTATCT ... (Lee et al., *Biol. Chem.* 266, 16188 (1991); Dorfmann et al., *J. Biol. Chem.* 267, 1279 (1992) and Wilson et al., *Mol. Cell. Biol.* 10, 4854 (1990)).

b) Activator Sequences, Activated in Glial Cells

A preferred activator sequence is furthermore to be understood as being a nucleotide sequence (promoter sequence or enhancer sequence) which interact with transcription factors which are formed to a particularly great extent, or are active, in glial cells.

These activator sequences include, in particular, gene-regulatory sequences or elements from genes which, for example, encode the following proteins which can be detected in glial cells:

The Schwann cell-specific protein periaxin
(Gillespie et al., *Neuron* 12, 497 (1994)) The promoter sequences have been described by Gillespie et al., (*Neuron* 12, 497 (1994)).

Glutamine synthetase
(Akimoto et al., *Brain Res.* 72, 9 (1993), Fressinaud et al., *J. Cell Physiol.* 149, 459 (1991)).
The promoter sequences have been described by Chakrabarti et al. (*Gene* 153, 163 (1995)) and Bhandarie et al., (*J. Biol. Chem.* 266, 7784 (1991)).

The glial cell-specific protein
(Glial fibrillary acidic protein=GFAP) (Akimoto et al., *Brain Res.* 72, 9 (1993))
The promoter sequences have been described by Kumanishi et al. (*Acta Neuropath.* 83, 569 (1992)), Besuard et al. (*J. Biol. Chem.* 266, 18877 (1991)), Reeves et al. (*PNAS USA* 86, 5178 (1989)), Brenner et al. (*Brain Res.* 7, 277 (1990)) and Masood et al. (*J. Neurochem.* 61, 160 (1993)).

The S100b glial cell protein
(Shen et al., *Mol. Brain Res.* 21, 62 (1994)) The promoter sequence has been described by Zimmer et al., (*Brain Res. Bulletin* 37, 417 (1995)).

IL-6 (CNTF)
(Sparacio et al., *J. Neuroimmunol.* 39, 231 (1992))
The promoter sequences have been described by Chernajoosky et al. (*J. Cell. Biochem. Suppl.* 0/13, 73 (1989)), Ray et al. (*Mol. Cell Biol.* 10, 5736 (1990)), Droogmans et al. (*DNA Sequence* 3, 115 (1992)), Mori et al. (*Blood* 84, 2904 (1994)), Liberman et al. (*Mol. Cell. Biol.* 10, 2327 (1990)) and Ishiki et al. (*Mol. Cell. Biol.* 10, 2757 (1990)).

5-HT receptors
(Whitaker-Azmitia et al., *Synapse* 14, 201 (1993)) The promoter sequences have been described by Elliott et al. (*Neurochem. Int.* 25, 537 (1994)), Veldman et al. (*Mol. Pharmac.* 42, 439 (1992)), Adham et al. (*PNAS USA* 90, 408 (1993)), Mochizuki et al. (*BBRC* 185, 517 (1992)) and Jin et al. (*J. Biol. Chem.* 267, 5735 (1992)).

TNFα
(Perez et al., *Cell* 63, 251 (1990), Merrill et al., *J. Immunol.* 151, 2132 (1993)).
The promoter sequences have been described by Takashiba et al. (*Gene* 131, 307 (1993)) and van der Ahe et al. (*Nucl. Acids Res.* 21, 5636 (1993)).

IL-10
  (Owens et al., *Immunol. Today* 15, 566 (1994)). The promoter sequences have been described by Kim et al. (*J. Immunol.* 148, 3618 (1992)), Kube et al. (*Cytokine* 7, 1 (1995) and Platzer et al. (DNA-Sequence 4, 399 (1994)).

Insulin-like growth factor receptor I and II
  The promoter sequences have been described by Morgan et al. (*Nature* 329, 301 (1987)), Cooke et al. (*BBRC* 177, 1113 (1991)), Kim et al. (*Mol. Endocrin.* 5, 1964 (1991)), van Dijk et al. (*Mol. Cell. Endocrin.* 81, 81 (1991)), Raizis et al. (*Biochem. J.* 289, 133 (1993)) and Yu et al. (*Nature* 371, 714 (1994)).

VEGF
  VEGF is formed in vascularized tissue, particularly under hypoxic conditions (Berse et al., *Mol. Biol. Cell* 3, 211 (1992), Finkenzeller et al., *BBRC* 208, 432 (1995), Tischer et al., *BBRC* 165, 1198 (1989), Leung et al., *Science* 246, 1306 (1989), Ferrara et al., *Endoc. Rev.* 13, 18 (1992)). The gene-regulatory sequence for the VEGF gene is
  The promoter sequence of VEGF (5' flanking region) Michenko et al., *Cell Mol. Biol. Res.* 40, 35 (1994), Tischer et al., *J. Biol. Chem.* 266, 11947 (1991) or
  the enhancer sequence of the VEGF gene (3' flanking region)
   (Michenko et al., *Cell Mol. Biol. Res.* 40, 35 (1994)) or
  the c-Src gene
   (Mukhopadhyay et al., *Nature* 375, 577 (1995), Bonham et al., *Oncogene* 8, 1973 (1993), Parker et al., *Mol. Cell. Biol.* 5, 831 (1985), Anderson et al., *Mol. Cell. Biol.* 5, 1122 (1985)) or
  the v-Src gene
   (Mukhodpadhyay et al., *Nature* 375, 577 (1995), Anderson et al., *Mol. Cell. Biol.* 5, 1122 (1985), Gibbs et al., *J. Virol.* 53, 19 (1985))

2.2 Choice of the Promoter Module

A cell cycle-regulated promotor module is, for example, to be understood as being the nucleotide sequence —CDE—CHR—Inr—. The essential function of the promotor module is to inhibit the function of the activator sequence in the G0/G1 phase of the cell cycle and to ensure cell cycle-specific expression in the S/G2 phase, and consequently in proliferating cells.

The promoter module CDE—CHR—Inr was discovered in the context of a detailed investigation of the G2-specific expression of the human cdc25C promoter. The starting point was finding a regulatory element ("cell cycle dependent element"; CDE) which is responsible for switching off the promoter in the G1 phase of the cell cycle (Lucibello et al., *EMBO J.* 14, 132 (1995)). Using genomic dimethyl sulfate (DMS) footprinting and functional analyses (FIGS. 1 and 2), it was demonstrated that the CDE binds a repressor ("CDE-binding factor"; CDF) in a G1-specific manner and thereby leads to inhibition of transcription in non-proliferating (G0) cells. The CDE, which is located within the region of the basal promoter, is dependent, in its repressing function, on an "upstream activating sequence" (UAS).

This led to the conclusion that the CDE-binding factor inhibits the transcription-activating effect of 5'-bound activator proteins in a cell cycle-dependent manner, i.e. in non-proliferating cells and in the G1 phase of the cell cycle (FIG. 3).

Figure 4:
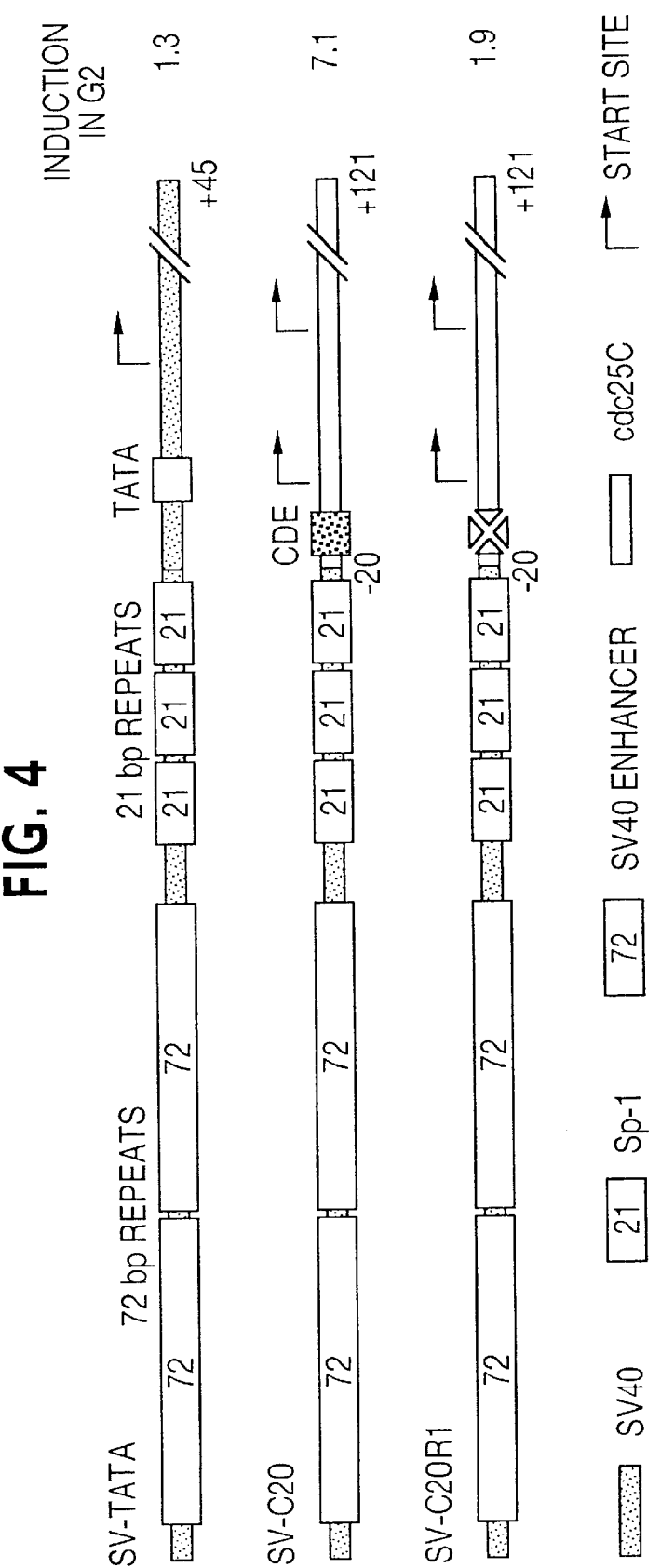
FIG. 4: $G_0/G_1$-specific repression of the SV40 enhancer by the CDE.

This conclusion was confirmed by a further experiment: fusion of the viral, non-cell cycle-regulated early SV40 enhancer to a cdc25 minimum promoter (composed of CDE and the 3' situated start sites) led to clear cell cycle regulation of the chimeric promoter (FIG. 4). Subsequent examination of the cdc25C enhancer has demonstrated that the transcription factors which are regulated by the CDF in a cell cycle-dependent manner are NF-Y (CBF) (Dorn et al., *Cell* 50, 863 (1987), van Hujisduijnen et al., *EMBO J.* 9, 3119 (1990), Coustry et al., *J. Biol. Chem.* 270, 468 (1995)), Sp1 (Kadonaga et al., *TIBS* 11, 10 (1986)) and a transcription factor (CIF) which is possibly novel and which binds to CBS7. Another interesting finding of this study was the observation that NF-Y only activates transcription efficiently within the cdc25C enhancer in cooperation with at least one further NF-Y complex or with CIF. Both NF-Y and Sp1 belong to the glutamine-rich activator class, which provides important indications with regard to the mechanism of the repression (e.g. interaction or interference with particular basal transcription factors or TAFs).

Figure 5:
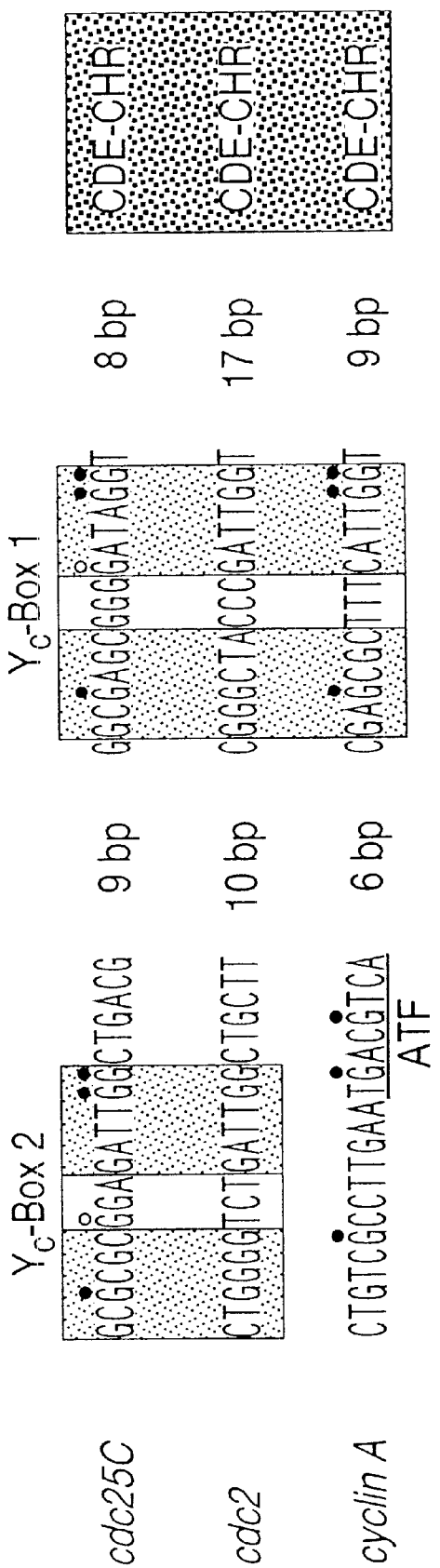
FIG. 5: Homologies in the CDE-CHR region and the 5'-situated Yc boxes in the cdc25C, cyclin A and cdc2 promoters. SEQ ID NOS: 1–2, 5–6, and 3–4, respectively.

A comparison of the promoter sequences of cdc25C, cyclin A and cdc2 demonstrated homologies in several regions (FIG. 5). This is not only the CDE, but also the adjacent Yc boxes, which are conserved in all 3 promoters (the divergences which exist are not functionally relevant). As expected, all these regions exhibited protein binding in vivo, with this protein binding taking place in a cell cycle-dependent manner in the case of the CDE. In addition, it was demonstrated that all 3 promoters are deregulated by a mutation of the CDE (Table 2). A remarkable similarity was also evident when comparing the cdc25C, cyclin A and cdc2 sequences in the region immediately 3' of the CDE ("cell cycle genes homology region"; CHR) (FIG. 5). While this region is functionally as important as the CDE (Table 2), it is not visible in the in-vivo DMS footprinting experiments.

A possible explanation for this is an interaction of the factor with the minor groove of the DNA. Results of "electrophoretic mobility shift assay" (EMSA) experiments indicate that CDE and CHR together bind a protein complex, the CDF. These observations suggest the conclusion that CDF-mediated repression of glutamine-rich activators is a frequently occurring mechanism of cell cycle-regulated transcription.

However, it is apparently not only the CDE-CHR region which is of importance for regulating the cdc25C promoter but also one of the initiation sites (position +1) within the nucleotide sequence of the basal promoter (positions $\leq-20$ to $\geq+30$, see FIG. 1). Mutations in this region, which encompasses the in-vitro binding site for the transcription factor YY-1 (Seto et al., *Nature* 354, 241 (1991), Usheva and Shenk *Cell* 76, 1115 (1994)), lead to complete deregulation. In view of the proximity of the CDE—CHR to the basal promoter, interaction of the CDF with the basal transcription complex is consequently very probable.

2.3. Choice of the Neurospecific Factor a) Neuronal Growth Factors

Within the meaning of the invention, a neurospecific factor is to be understood as being a DNA sequence which encodes a neuronal growth factor. By way of example, these neuronal growth factors include, in particular:

FGF
  (Johnson et al., *Adv. Cancer Rec.* 60, 1 (1993), Jay et al., *Science* 233, 541 (1986), Abrahahm et al., *EMBO J.* 5, 2523 (1986), *Science* 233, 545 (1986), Mergia et al., *BBRC* 138, 644 (1986), Schweigerer, *Nature* 325, 257 (1987), PNAS USA 84, 842 (1987))

Nerve growth factor (NGF)
  (Haktzopoulous et al., *Neuron* 13, 187 (1994), Takeda et al., *Neuroscience* 55, 23 (1993), Cartwright et al., *Brain Res.* 15, 67 (1992))

Brain-derived neurotrophic factor (BDNF)
(Zhang et al., *J. Neurobiol.* 25, 1517 (1994), Maisonpierre et al., *Genomics* 10, 558 (1991), DNA Sequence 3, 49 (1992), Timmusk et al., *Neuron* 10, 475 (1993)).

Neurotrophin-3 (NT-3)
(Hallboeoek et al., *Eur. J. Neurosci.* 5, 1 (1993), Rodriguez-Tebar et al., *Philiosoph. Transact. Roy. Soc. Biol. Sci.* 331, 255 (1991), Leingärtner et al., *Eur. J. Neurosci.* 6, 1149 (1994))

Neurotrophin-4 (NT-4)
(Ibanez et al., *PNAS* 89, 3060 (1992), Ny et al., *PNAS* 89, 3060 (1992))

Ciliary neurotrophic factor (CNTF)
(Ishiki at al., *New Biologist* 3, 63 (1991), Ray et al., *Mol. Cell Biol.* 9, 5537 (1989), Leung et al., *Neuron* 8/6, 1045 (1992), Bootha et al., *Gene* 146, 303 (1994)).

b) Enzymes

In addition, a neurospecific factor is to be understood as being a cDNA sequence which encodes:

tyrosine hydroxylase
(Goc et al., *Mol Cell Neurosci.* 3, 383 (1992), Boularand et al., *J. Biol. Chemistry* 270, 3748 (1995)) or dopa decarboxylase
(Maras et al., *Eur. J. Biochem.* 201, 385 (1991), Nayatsu, *Neurosci. Res.* 12, 315 (1991), Ichinose et al., *Biochem.* 31, 11546 (1992), Levanthai et al., *Mol. Brain Res.* 17, 227 (1993), Sumiichinose et al., *J. Neurochem.* 64, 514 (1995)).

c) Cytokines and Their Inhibitors

A neurospecific factor is furthermore to be understood as being a DNA sequence which encodes proteins which inhibit or neutralize the neurotoxic effect of TNFα. These proteins include, for example:

TGFβ
(Massague, *Ann. Rev. Cell. Biol.* 6, 597 (1990), Kondiah et al., *J. Biol. Chem.* 265, 1089 (1990), Garnier et al., *J. Mol. Biol.* 120, 97 (1978)). TGFβ inhibits TNFα-mediated cytotoxicity (Merrill et al., *J. Immunol.* 151, 2132 (1993), Quin et al., *Annals of Surgery* 220, 508 (1994))

Soluble TNF receptors
(Nophar et al., *EMBO J.* 9, 3269 (1990), Himmler et al., *DNA Cell Biol.* 9, 705 (1990), Aggarwal et al., *Nature* 318, 665 (1985), Gray et al., *PNAS* 87, 7380 (1990), Tartaglia et al., *Immunol. Today* 13, 151 (1992), Loetcher et al., *Cell* 61, 351 (1990), Schall et al., *Cell* 61, 361 (1990), Smith et al., *Science* 248, 1019 (1990), Goodwin et al., *Mol. Cell. Biol.* 11, 3020 (1991)).

TNF receptors neutralize TNFα. Review: Olsson et al., *Eur. Cytokine Netw.* 4, 169 (1993).

IL-10
(Moore et al., *Science* 248, 1230 (1990), Vieira et al., *PNAS USA* 88, 1172 (1991), Kim et al., *J. Immunol.* 148, 3618 (1992)).

IL-10 inhibits the formation of IFN gamma, TNFα, IL-2 and IL-4 (Schlaak et al., *Scand. J. Immunol.* 39, 209 (1994), Vieira et al., *PNAS USA* 88, 1172 (1991), Benjamin et al., *Leuk. Lymph.* 12, 205 (1994))

soluble IL-1 receptors
IL-1 receptor I
(Sims et al., *PNAS USA* 86, 8946 (1989), Dower et al., *J. Exp. Med.* 162, 501 (1985), Chizzonite et al., *PNAS* 86, 8029 (1989)

IL-1 receptor II
(McMahan et al., *EMBO J.* 10, 2821 (1991), Sims et al., *Science* 241, 585 (1988)).

Soluble IL-1 receptors neutralize the activity of IL-1 (Colotta et al., *Immunol. Today* 15, 562 (1994), Sims et al., *Clin. Immunol. Immunopath.* 72, 9 1994))

IL-1 receptor antagonist
(Eisenberg et al., *Nature* 343, 341 (1990), Carter et al., Nature 344 (633 (1990))

soluble IL-6 receptors
(Mackiewicz et al., *Cytokine* 7, 142 (1995))

However, within the meaning of the invention, DNA sequences of fusion proteins formed between the listed cytokines and growth factors, or the extracellular moiety of the receptors, on the one hand, and the Fc moiety of human immunoglobulin, on the other hand, can also be used as the active substance. DNA sequences of this nature, and their preparation have been described in EP 0 464 533 A1.

2.4. Combination of Several Neurospecific Factors

The invention furthermore relates to an active compound in which a combination of the DNA sequences of identical neurospecific factors (A,A) or different neurospecific factors (A,B) is present. The CDNA of an "internal ribosome entry site" (IRES) is preferably interpolated, as a regulatory element, for the purpose of expressing two DNA sequences.

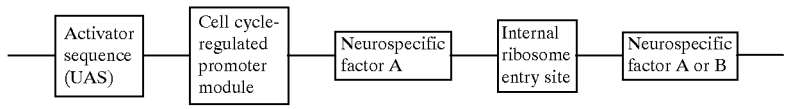

IRESs of this nature have, for example, been described by Montford and Smith (TIG 11, 179 (1995), Kaufman et al., *Nucl. Acids Res.* 19, 4485 (1991), Morgan et al., *Nucl. Acids Res.* 20, 1293 (1992, Dirks et al., *Gene* 128, 247 (1993), Pelletier and Sonenberg, *Nature* 334, 320 (1988) and Sugitomo et al., *BioTechn.* 12, 694 (1994).

Thus, the cDNA of the IRES sequence of poliovirus (position $_{13}$ <140 to __>630 of the 5' UTR (Pelletier and Sonenberg, *Nature* 334, 320 (1988)) can be used for linking the DNA of antiinflammatory substance A (at the 3' end) and the DNA of antiinflammatory substance B (at the 5' terminus).

Depending on the combination, an active compound of this nature exhibits either an additive (A+A, A+B1) or a synergistic effect within the meaning of the invention.

2.5. Construction of the Vector

The novel DNA construct is made into a vector in a manner familiar to the skilled person. This vector can be of viral or non-viral origin. For example, the novel DNA construct is inserted into a viral vector (in this regard, see D. Jolly, *Cancer Gene Therapy* 1, 51 (1994)), or else completed to form a plasmid. Viral vectors or plasmids can be complexed with collodial dispersions. These dispersions include, for example, liposomes (Farhood et al., *Annals of the New York Academy of Sciences* 716, 23 (1994)) or else polylysine/ligand conjugates (Curiel et al., *Annals of the New York Academy of Sciences* 716, 36 (1994)).

2.6. Choice of the Ligands

Viral and non-viral vectors can be supplemented with a ligand. Substances which bind to the surface of endothelial cells are preferred as ligand, for example in polylysine/ligand conjugates. These substances include antibodies or antibody fragments which are directed against membrane structures of endothelial cells, as described, for example, by Burrows et al. (*Pharmac. Ther.* 64, 155 (1994)) or in EP 0 408 859 A2. In particular, these substances include antibodies against the VEGF receptors.

The murine monoclonal antibodies should preferably be employed in humanized form. The humanization is effected in the manner described by Winter et al. (*Nature* 349, 293 (1991) and Hoogenboom et al. (*Rev. Tr. Transfus. Hemobiol.* 36, 19 (1993). Antibody fragments are prepared in accordance with the state of the art, for example in the manner described by Winter et al., *Nature* 349, 293 (1991), Hoogenboom et al., *Rev. Tr. Transfus. Hemobiol.* 36, 19 (1993), Givol, *Mol. Immunol.* 28, 1379 (1991) or Huston et al., *Int. Rev. Immunol.* 10, 195 (1993).

These substances additionally include all active compounds which bind to membrane structures or membrane receptors on endothelial cells. For example, the active compounds include growth factors, or their fragments or constituent sequences thereof, which bind to receptors which are expressed by endothelial cells, such as, for example, PDGF, bFGF, VEGF and TGFβ (Pusztai et al., *J. Pathol.* 169, 191 (1993)). In addition, these substances include substances which carry mannose terminally and bind to the mannose 6-phosphate receptor of endothelial cells (Perales et al., *Eur. J. Biochem.* 226, 225 (1994)).

In addition, these substances include adhesion molecules which bind to activated and/or proliferating endothelial cells. Adhesion molecules of this nature, such as SLeX, LFA-1, MAC-1, LECAM-1 or VLA-4, have already been described (reviews in Augustin-Voss et al., *J. Cell Biol.* 119, 483 (1992), Pauli et al., *Cancer Metast. Rev.* 9, 175 (1990), Honn et al., *Cancer Metast. Rev.* 11, 353 (1992)).

In addition, substances which bind to the surface of glial cells are to be regarded as ligands.

These substances include antibodies or antibody fragments which are directed against membrane structures of glial cells, as reported, for example, by Mirsky et al., (*Cell and Tissue Res.* 240, 723 (1985) by Coakham et al., (*Prog. Exp. Tumor Rex.* 29, 57 (1985)) and by McKeever et al. (*Neurobiol.* 6, 119 (1991)). These membrane structures additionally include neural adhesion molecules such as N-CAM, in particular its polypeptide chain C (Nybroe et al., *J. Cell Biol.* 101, 2310 (1985)).

These substances additionally include all active compounds which bind to membrane structures or membrane receptors on glial cells. For example, these substances include substances which carry mannose terminally and which bind to the mannose 6-phosphate receptor (Perales et al., *Eur. J. Biochem.* 226, 225 (1994), insulin and insulin-like growth factor (Merrill et al., *J. Clin. Endocrin. Metab.* 71, 199 (1990)), PDGF (Ek et al., *Nature* 295, 419 (1982)) and those fragments of these growth factors which bind to the relevant membrane receptors.

2.7. Preparation of the Active Compound

Preparation of the novel active compound is described in more detail with the aid of the following example:

a) Construction of the Chimeric Promoter Endothelin 1 CDE—CHR—Inr

Figure 6:
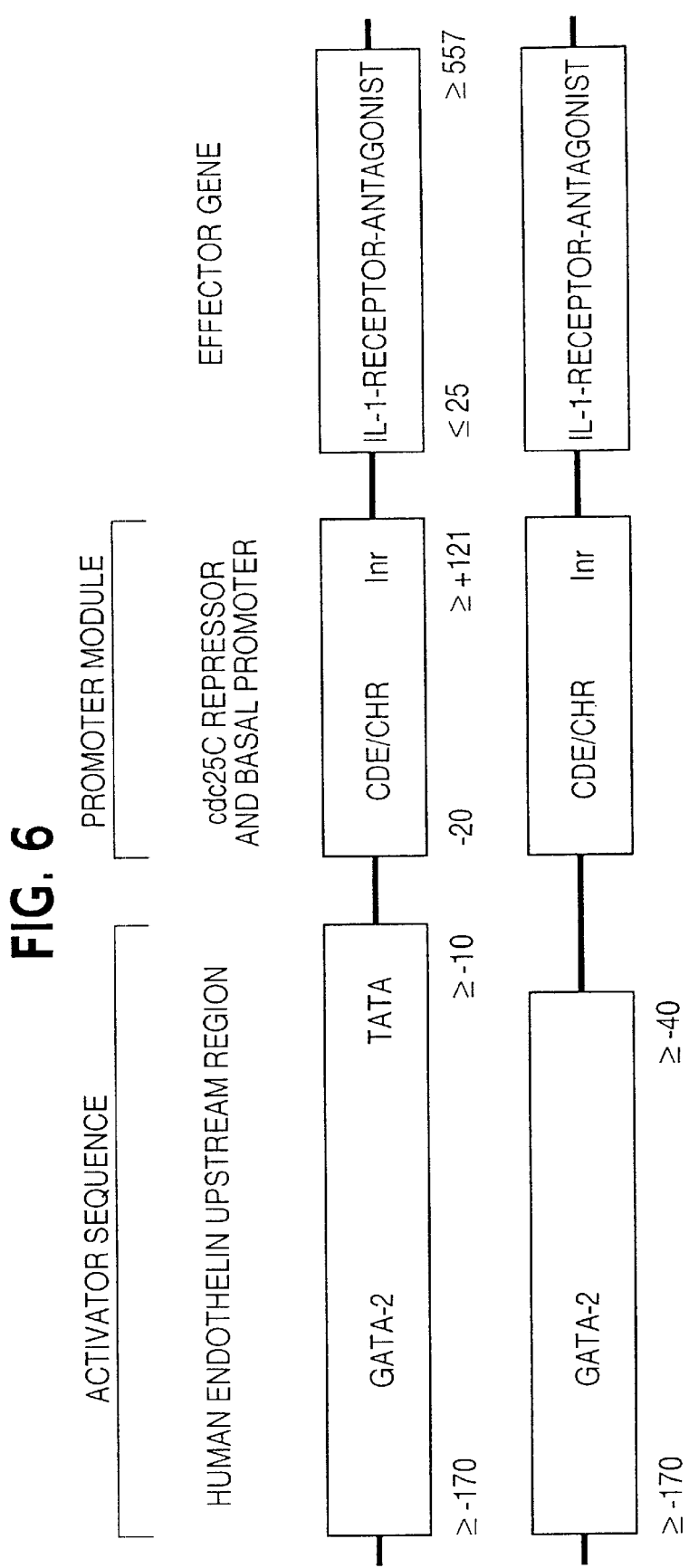
FIG. 6: Chimeric constructs composed of different moieties of the human endothelin-1 promoter, the 3'-fused promoter module containing the CDE and CHR repressor elements, and also a DNA for the IL-1 receptor antagonist (complete coding region, position ≦25 to ≧557; Eisenberg et al., *Nature* 343: 341 (1989)), as effector. Position indications relate to the data of Wilson et al., *Mol. Cell. Biol.*, 10: 4854 (1990) for the endothelin-1 gene or to the system used by Lucibello et al., *EMBO J.* 14: 132 (1995) for cdc25C.

The human endothelin-1 promoter (position $\leq -170$ to $\geq -10$), or a variant which is truncated by the TATA box (position $\leq -170$ to $\geq -40$), is linked, at its 3' end, to the 5' terminus of the CDE—CHR—Inr module (position $\leq -20$ to $\geq +121$) of the human cdc25C gene (FIG. 6). The linking is effected using enzymes which are known to the skilled person and which are commercially available.

b) Construction of a Plasmid which Contains the Central Component of the Active Compound The chimeric endothelin-1 repressor module transcription unit which has been prepared in this way is linked at its 3' ends to the 5' terminus of a DNA which contains the complete coding region of the IL-1 receptor antagonist 152 amino acids in length (DNA position $\leq 25$ to $\geq 557$; Eisenberg et al., *Nature* 343, 341 (1990)). This DNA also contains the signal sequence (25 N-terminal amino acids) which is necessary for secretion. Transcription control units and IL-1 receptor antagonist DNA are cloned into pUC19/19 or Bluescript-derived plasmid vectors which can be used, either directly (Yovandich et al., *Hum. Gene Ther.* 6 603 (1995)) or in colloidal dispersion systems, for an in-vivo transfer.

Alternatively, the transcription control units and IL-1 receptor antagonist DNA which have been joined together can be transferred into viral vectors or other non-viral vectors which are familiar to the skilled person.

2.8. Activity of the Active Compound

Following local administration, for example at the site of the nerve damage or intracranial or subarachnoid administration, or systemic, preferably intravenous or intraarterial, administration, an active compound according to the present invention enables, by means of the tissue-specific enhancer and the basal promoter, endothelial cells, which are mainly, if not exclusively, only proliferating cells, or proliferating glial cells to secrete neurospecific factors. Endothelial cell proliferations or glial cell proliferations of this nature are to be expected in the region and as a reaction to tissue damage which has concomitantly also caused the nerve damage. The novel active compound consequently ensures a high concentration of the neurospecific factor at the site of the nerve damage.

Since the active compound promises a high degree of safety, both on account of its cell specificity and its cell cycle specificity, it can also be used for the prophylaxis or therapy of nerve damage in high doses and, if necessary, repeatedly at intervals of days or weeks.

TABLE 1

| Neuronal growth factors | | |
|---|---|---|
| | Site of formation | Site of action |
| Epidermal growth factor family | | |
| Schwannoma-derived growth factor (SDGF) | Schwann cells | Astrocytes Schwann cells Fibroblasts |
| Heparin binding growth factor family | | |
| acidic fibroblast growth factor (aFGF) | ubiquitous | ubiquitous |
| basic fibroblast growth factor (bFGF) | ubiquitous | ubiquitous |
| Nerve growth | | |

TABLE 1-continued

Neuronal growth factors

| factor family | Site of formation | Site of action |
|---|---|---|
| nerve growth factor (NGF) | Schwann cells Neurones Melanocytes Cholinergic neurones in the brain | Peripheral neurones |
| brain derived neurotrophic factor (BDNF) | Neurones Glial cells | Dopaminergic neurones in the brain |
| Neurotrophin-3, -4 (NT-3, NT-4) | many cell types | Peripheral proprioceptive neurones |
| Ciliary neurotrophic factor (CNTF) | | Peripheral nerve cells |

TABLE 2

Role of CDE and CHR in the cell cycle-regulated transcription of cdc25C, cyclin A and cdc2
Tab. 2

|  | $G_0$ | Growing | Factor |
|---|---|---|---|
| wt |  |  |  |
| cdc25C | 0.8 | 13.1 | 17.5 |
| cyclin A | 0.7 | 27.1 | 41.7 |
| cdc2 | 1.0 | 41.2 | 41.2 |
| mCDE (−13) |  |  |  |
| cdc25C | 7.6 | 11.6 | 1.5 |
| cyclin A | 13.4 | 23.9 | 1.8 |
| cdc2 | 11.3 | 33.9 | 3.0 |
| mCHR (−6/−3) |  |  |  |
| cdc25C | 14.4 | 21.0 | 1.5 |
| cyclin A | 15.5 | 28.3 | 1.8 |
| cdc2 | 18.6 | 38.6 | 2.1 |

The results of transient transfections in HIH3T3 cells are presented as RLUs/1000.

mCDE: mutated CDE (pos. −13: G → T); mCHR: mutated CHR (pos. −6 to −3).

What is claimed is:

1. A DNA construct, which comprises, in 5' to 3' order: an activator sequence, a cell cycle-regulated promoter module and a polynucleotide encoding a polypeptide selected from the group consisting of a neuronal growth factor, Schwanoma-derived growth factor, basic fibroblast growth factor, acidic fibroblast growth factor, nerve growth factor, brain-derived neurotrophic factor, neurotrophin-3, neurotrophin-4, ciliary neurotrophic factor, a tyrosine hydroxylase, dopa decarboxylase, transforming growth factor-β, a soluble tumor necrosis factor receptor, interleukin-10, a soluble interleukin-1 receptor, an interleukin-1 receptor antagonist, a soluble interleukin-6 receptor, a fusion protein comprising a cytokine and the Fc moiety of human immunoglobulin, and a fusion protein comprising the extracellular moiety of a cytokine receptor and the Fc moiety of human immunoglobulin.

2. The DNA construct of claim 1, wherein said promoter module comprises the DNA sequence of base 291 through base 340 of SEQ ID NO:7.

3. The DNA construct of claim 1, wherein the cell cycle dependent element of said promoter module comprises the nucleotide sequence TGGCGG.

4. The DNA construct of claim 1, wherein the cell cycle gene homology region of said promoter module comprises the nucleotide sequence GTTTGAA.

5. The DNA construct of claim 1, wherein said activator sequence is selected from the group consisting of: a CMV promoter, a CMV enhancer and a SV40 promoter.

6. The DNA construct of claim 1, wherein said activator sequence is a promoter for a gene encoding a protein selected from the group consisting of brain-specific endothelial glucose-1 transporter, endoglin, VEGF receptor 1, VEGF receptor 2, receptor tyrosine kinase til-1, receptor tyrosine kinase til-2, B61 receptor, endothelin B, endothelin 1, an endothelin receptor, mannose 6-phosphate receptor, IL-1α receptor, IL-1β receptor, IL-1 receptor, VCAM-1, and von Willebrand factor.

7. The DNA construct of claim 1, wherein said activator sequence comprises an oligomer of the binding site for a transcription factor, wherein said factor is preferentially active in endothelial cells.

8. The DNA construct of claim 7, wherein said binding site comprises the sequence 5'-TTATCT-3'.

9. The DNA construct of claim 1, wherein said activator sequence is a promoter for a gene encoding a protein selected from the group consisting of Schwann cell-specific periaxin, glutamine synthetase, glial-specific protein, glial cell protein S100b, interleukin-6, a 5-hydroxytryptamine receptor, TNFα, IL-10, and insulin-like growth factor receptor.

10. The DNA construct of claim 1, wherein said activator sequence is selected from the group consisting of a promoter for a VEGF gene, an enhancer sequence for a VEGF gene, a v-Src gene, and a c-Src gene.

11. A vector comprising the DNA construct of claim 1.

12. The vector of claim 11, wherein the vector is a virus.

13. The vector of claim 12, wherein the virus is selected from the group consisting of retrovirus, adenovirus, adeno-associated virus, herpes simplex virus and vaccinia virus.

14. A plasmid comprising the DNA construct of claim 1.

15. The DNA construct of claim 1, comprising, in 5' to 3' order, an activator sequence, a cell cycle-regulated promoter module, a first polynucleotide, an internal ribosome entry site, and a second polynucleotide, wherein said first and second polynucleotides each encode polypeptides independently selected from the group consisting of a neuronal growth factor, Schwanoma-derived growth factor, basic fibroblast growth factor, acidic fibroblast growth factor, nerve growth factor, brain-derived neurotrophic factor, neurotrophin-3, neurotrophin-4, ciliary neurotrophic factor, a tyrosine hydroxylase, dopa decarboxylase, transforming growth factor-β, a soluble tumor necrosis factor receptor, interleukin-10, a soluble interleukin-1 receptor, an interleukin-1 receptor antagonist, a soluble interleukin-6 receptor, a fusion protein comprising a cytokine and the Fc moiety of human immunoglobulin, and a fusion protein comprising the extracellular moiety of a cytokine receptor and the Fc moiety of human immunoglobulin.

16. A DNA construct, which comprises, in 5' to 3' order: an activator sequence, a cell cycle-regulated promoter module and a polynucleotide encoding a polypeptide selected from the group consisting of a neurotrophic factor, epidermal growth factor, heparin binding growth factor, a fusion protein comprising a growth factor and the Fc moiety of human immunoglobulin, and a fusion protein comprising the extracellular moiety of a growth factor receptor and the Fc moiety of human immunoglobulin.

* * * * *